US011123656B2

United States Patent
Sasuga et al.

(10) Patent No.: US 11,123,656 B2
(45) Date of Patent: Sep. 21, 2021

(54) SEPARATION/ANALYSIS METHOD FOR MIXTURE OF OLIGONUCLEOTIDES

(71) Applicant: SHOWA DENKO K.K., Tokyo (JP)

(72) Inventors: Junji Sasuga, Tokyo (JP); Hirobumi Aoki, Tokyo (JP); Yuzuru Kokido, Tokyo (JP)

(73) Assignee: SHOWA DENKO K.K., Tokyo (JP)

( * ) Notice: Subject to any disclaimer, the term of this patent is extended or adjusted under 35 U.S.C. 154(b) by 0 days.

(21) Appl. No.: 16/609,938

(22) PCT Filed: Jun. 21, 2018

(86) PCT No.: PCT/JP2018/023650
§ 371 (c)(1),
(2) Date: Oct. 31, 2019

(87) PCT Pub. No.: WO2018/235904
PCT Pub. Date: Dec. 27, 2018

(65) Prior Publication Data
US 2020/0054966 A1 Feb. 20, 2020

(30) Foreign Application Priority Data
Jun. 22, 2017 (JP) .............................. JP2017-122345

(51) Int. Cl.
*B01D 15/32* (2006.01)
*B01J 20/285* (2006.01)
(Continued)

(52) U.S. Cl.
CPC ........... *B01D 15/32* (2013.01); *B01D 15/166* (2013.01); *B01D 15/20* (2013.01); *B01D 15/424* (2013.01);
(Continued)

(58) Field of Classification Search
CPC ...... B01D 15/32; B01D 15/166; B01D 15/20; B01D 15/424; B01J 20/285; B01J 20/281;
(Continued)

(56) References Cited

U.S. PATENT DOCUMENTS

| 4,447,559 A | 5/1984 | Hanaoka et al. |
| 5,503,933 A * | 4/1996 | Afeyan .................. B01D 15/08 210/198.2 |

(Continued)

FOREIGN PATENT DOCUMENTS

| CN | 101274272 A | 10/2008 |
| CN | 104826618 A | 8/2015 |

(Continued)

OTHER PUBLICATIONS

Ji et al. A polyvinyl alcohol-coated silica gel stationary phase for hydrophilic interaction chromatography. Analyst, 2015, 140, 6250. (Year: 2015).*

(Continued)

*Primary Examiner* — Katherine Zalasky McDonald
(74) *Attorney, Agent, or Firm* — Sughrue Mion, PLLC

(57) ABSTRACT

The present invention relates to a method of separating and analyzing a mixture of oligonucleotides, including performing liquid chromatography using a column packed with a packing material obtained by fixing a diol to a surface of each of porous particles formed of a crosslinked organic polymer. According to this method, the oligonucleotides can be separated and analyzed with higher sensitivity compared to cases where columns having silica gel as a base material are used. In addition, the column can be washed with an alkaline solution.

8 Claims, 2 Drawing Sheets

(51) Int. Cl.

| | | |
|---|---|---|
| *G01N 30/34* | (2006.01) | |
| *G01N 30/50* | (2006.01) | |
| *G01N 30/72* | (2006.01) | |
| *G01N 30/74* | (2006.01) | |
| *G01N 30/88* | (2006.01) | |
| *B01D 15/16* | (2006.01) | |
| *B01D 15/42* | (2006.01) | |
| *B01D 15/20* | (2006.01) | |
| *B01J 20/32* | (2006.01) | |
| *C07K 1/20* | (2006.01) | |
| *B01J 20/28* | (2006.01) | |

(52) U.S. Cl.
CPC ......... *B01J 20/285* (2013.01); *B01J 20/3246* (2013.01); *C07K 1/20* (2013.01); *G01N 30/34* (2013.01); *G01N 30/50* (2013.01); *G01N 30/72* (2013.01); *G01N 30/74* (2013.01); *G01N 30/88* (2013.01); *B01J 20/28016* (2013.01)

(58) Field of Classification Search
CPC .. B01J 20/3208; B01J 20/321; B01J 20/3246; B01J 20/28016; G01N 30/26; G01N 30/28; G01N 30/34; G01N 30/48; G01N 30/482; G01N 30/62; G01N 30/72; G01N 30/50; G01N 30/74
See application file for complete search history.

(56) References Cited

U.S. PATENT DOCUMENTS

| | | | | |
|---|---|---|---|---|
| 6,090,288 | A * | 7/2000 | Berglund | B01D 15/363 210/198.2 |
| 2005/0153926 | A1 * | 7/2005 | Adams | C12N 15/87 514/44 R |
| 2005/0178730 | A1 | 8/2005 | Li | |
| 2005/0222279 | A1 * | 10/2005 | Larsson | B01J 20/26 521/50 |
| 2008/0293959 | A1 | 11/2008 | Liu et al. | |
| 2013/0236986 | A1 | 9/2013 | Case | |
| 2014/0005364 | A1 * | 1/2014 | Gottschall | B01J 20/3242 530/387.3 |
| 2014/0069870 | A1 * | 3/2014 | Pohl | B01J 20/288 210/656 |
| 2016/0046664 | A1 * | 2/2016 | Aldinger | B01J 20/264 530/416 |
| 2017/0007981 | A1 * | 1/2017 | Nakajima | B01J 20/34 |
| 2017/0205423 | A1 | 7/2017 | Higel et al. | |
| 2019/0184372 | A1 * | 6/2019 | Kato | B01J 20/281 |

FOREIGN PATENT DOCUMENTS

| | | | | |
|---|---|---|---|---|
| CN | 106457066 | A | | 2/2017 |
| EP | 3 019 861 | A1 | | 5/2016 |
| JP | 58-20235 | A | | 2/1983 |
| JP | 2007-522476 | A | | 8/2007 |
| JP | 2010-529431 | A | | 8/2010 |
| JP | 2016-524166 | A | | 8/2016 |
| WO | WO00/34343 | | * | 6/2000 |
| WO | 2015134317 | A1 | | 9/2015 |
| WO | WO-2015129622 | | * | 9/2015 |
| WO | 2016/009077 | A1 | | 1/2016 |
| WO | WO-2016051170 | A1 * | 4/2016 | ............ B01J 20/288 |
| WO | 2016/190043 | A1 | | 12/2016 |

OTHER PUBLICATIONS

Easter et al. Separation and identification of oligonucleotides by hydrophilic interaction liquid chromatography (HILIC)—inductively coupled plasma mass spectrometry (ICPMS). Analyst. Oct. 2010; 135(10): 2560-2565. (Year: 2010).*
Andrew J. Alpert et al., "Hydrophilic-Interaction Chromatography for the Separation of Peptides, Nucleic Acids and Other Polar Compounds", Journal of Chromatography, 1990, pp. 177-196, vol. 499.
Qin Li et al., "Comprehensive hydrophilic interaction and ion-pair reversed-phase liquid chromatography for analysis of di-to deca-oligonucleotides", Journal of Chromatography A, 2012, pp. 237-243, vol. 1255.
Sylwia Studzinska et al., "Application of hydrophilic interaction liquid chromatography coupled with mass spectrometry in the analysis of phosphorothioate oligonucleotides in serum", Journal of Chromatography B, 2017, pp. 282-288, vol. 1040.
International Search Report for PCT/JP2018/023650, dated Sep. 4, 2018.
Extended European Search Report dated Apr. 28, 2021 in European Application No. 18820716.1.
Petro et al., "Monodisperse Hydrolyzed Poly(glycidyl methacrylate-co-ethylene dimethacrylate) Beads as a Stationary Phase for Normal-Phase HPLC", Analytical Chemistry, 1997, vol. 69, pp. 3131-3139 (9 pages total).
Gong et al., "Preparation of Normal-Phase HPLC Stationary Phase Based on Monodisperse Hydrophilic Polymeric Beads and Their Application", Journal of Applied Polymer Science, 2007, vol. 106, pp. 2730-2735 (6 pages total).
Communication dated Jul. 6, 2021 by the China National Intellectual Property Administration in application No. 201880033534.0.

* cited by examiner

SEPARATION/ANALYSIS METHOD FOR MIXTURE OF OLIGONUCLEOTIDES

CROSS REFERENCE TO RELATED APPLICATIONS

This application is a National Stage of International Application No. PCT/JP2018/023650 filed Jun. 21, 2018, claiming priority based on Japanese Patent Application No. 2017-122345 filed Jun. 22, 2017.

TECHNICAL FIELD

The present invention relates to a method of separating and analyzing a mixture of oligonucleotides by liquid chromatography.

BACKGROUND ART

In recent years, application of synthetic oligonucleotides to a medical field has been attracting increasing attention. Examples thereof include ribozymes, aptamers, antisense oligonucleotides, and RNA interference (RNAi). Those oligonucleotides are called nucleotide drugs.

Such oligonucleotides are generally synthesized by a phosphoramidite method. Products in this method include, in addition to a target oligonucleotide, oligonucleotides having various chain lengths and impurities resulting from side reactions. Accordingly, various investigations have been made on a separation and analysis method for synthetic oligonucleotides.

A method based on hydrophilic interaction chromatography (HILIC) can be performed with an eluent containing a volatile salt at a low concentration. Accordingly, a mass spectrometer can be used as a detector, and hence high-sensitivity analysis is possible. In addition, also when separation is performed for the purpose of fractionating oligonucleotides, the method is excellent in that a step such as desalting in separation of the oligonucleotides from the eluent is facilitated.

In Non Patent Literature 1, there is a description of a method involving using an Ascentis Silica column from Sigma-Aldrich. This column uses a porous unmodified silica base having a diameter of 3 μm (pore size: 12 nm) as a packing material. It is reported that 2-mer to 10-mer synthetic oligonucleotides were highly separated by a gradient method involving using an ammonium formate buffer/acetonitrile mixed solution as an eluent and decreasing an acetonitrile concentration.

In addition, in Non Patent Literature 2, there is a description of a method involving using an Amide-80 column from Tosoh Corporation. This column contains a packing material in which an amide group-containing structure is bonded to a porous silica base having a diameter of 3 μm (pore size: 8 nm). It is reported that phosphorothioated 15-mer to 20-mer synthetic oligonucleotides were highly separated by using an aqueous ammonium formate solution/acetonitrile mixture as an eluent and applying a gradient in which an acetonitrile concentration is decreased.

CITATION LIST

Non Patent Literature

[NPL 1] Journal of Chromatography A, 1255 (2012) 237-243

[NPL 2] Journal of Chromatography B, 1040 (2017) 282-288

SUMMARY OF INVENTION

Technical Problem

A column packed with a related-art packing material utilizing a silica base cannot have an alkaline solution passed therethrough because the silica base is dissolved. Accordingly, the column cannot be subjected to washing with a strong alkali, particularly an aqueous sodium hydroxide solution, which is effective for: performance recovery through the removal of a protein, an oligonucleotide, a side reaction product, or the like at the time of a reduction in separation performance of the column due to the adsorption thereof; a reduction in carryover into an eluted fraction at the time of continuous use; sterilization of the column and an apparatus; and the like.

In addition, in consideration of further utilization of oligonucleotides in a medical field and the like, there is a demand for a more excellent separation and analysis method for oligonucleotides.

Therefore, an object of the present invention is to provide a method in which washing with an alkaline solution can be performed, and by which oligonucleotides can be separated and analyzed with high sensitivity.

Solution to Problem

The present invention provides the following separation and analysis method.

[1] A method of separating and analyzing a mixture of oligonucleotides, including performing liquid chromatography using a column packed with a packing material obtained by fixing a diol to a surface of each of porous particles formed of a crosslinked organic polymer.

[2] The method according to the above-mentioned item 1, wherein a structure of the diol includes a structure represented by the following formula (I):

$$R-O-CH_2-CH(OH)-CH_2(OH) \quad (I)$$

where R represents a partial structure of each of the porous particles.

[3] The method according to the above-mentioned item 1 or 2, wherein the crosslinked organic polymer is crosslinked polyvinyl alcohol.

[4] The method according to any one of the above-mentioned items 1 to 3, wherein a mobile phase (eluent) of the liquid chromatography is a mixed liquid of an aqueous solution of a volatile salt and a water-soluble organic solvent.

[5] The method according to any one of the above-mentioned items 1 to 4, further including detecting an eluted component separated through the column with an ultraviolet/visible detector and/or a mass spectrometer.

[6] The method according to any one of the above-mentioned items 1 to 5, wherein the liquid chromatography is performed by gradient elution of a mobile phase.

[7] The method according to any one of the above-mentioned items 1 to 6, further including, before or after the performing liquid chromatography, a step of washing the column by passing an alkaline solution having a pH of from 10.0 to 13.0 through the column.

[8] The method according to any one of the above-mentioned items 1 to 7, wherein the oligonucleotides are synthetic oligonucleotides.

Advantageous Effects of Invention

According to the present invention, the oligonucleotides can be separated and analyzed with higher sensitivity than by a method using a column utilizing a packing material utilizing a silica base.

In addition, an alkaline solution can be used for the washing of the column, and hence the washing and sterilization of the column can be simply performed, and moreover, the fractionation of oligonucleotides intended to be drugs is further facilitated.

DESCRIPTION OF EMBODIMENTS

Figure 1:
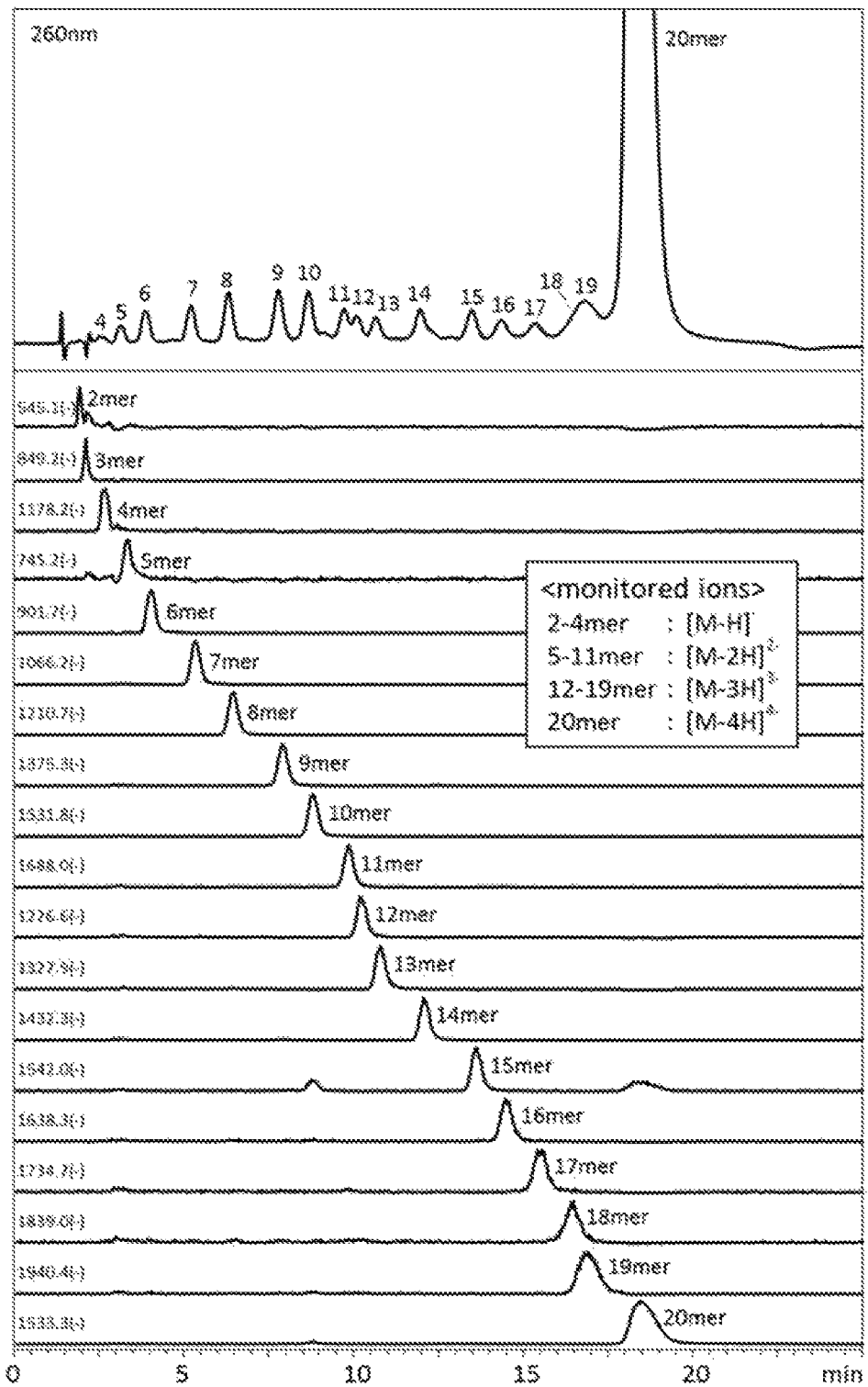
FIG. 1 are an ultraviolet detection (wavelength: 260 nm) chromatogram and a mass spectrometric mass chromatogram obtained in Example 1.

A separation and analysis method for a mixture of oligonucleotides according to one embodiment of the present invention is a method of separating and analyzing a mixture of oligonucleotides by liquid chromatography, and uses, as a packing material for a column for the liquid chromatography, one obtained by fixing a diol structure to a surface of each of porous particles formed of a crosslinked organic polymer.

The mixture of oligonucleotides is typically a reaction mixture obtained by the synthesis of oligonucleotides. The oligonucleotides are, for example, synthesized by allowing nucleotide monomers to continuously react on a solid support, and examples thereof include nucleotide oligomers synthesized by a phosphoramidite method. The target chain length of a synthetic oligonucleotide is from 10-mer to 110-mer. In the method according to the present invention, a 10- to 70-mer is preferably separated as a sample, and a 19- to 62-mer is more preferably separated.

The crosslinked organic polymer to be used as a base of the packing material for a column is preferably a crosslinked (meth)acrylic resin, crosslinked polyvinyl alcohol (PVA), or the like. When the crosslinked (meth)acrylic resin is used, its monomer units need to include a monomer unit having a hydroxy group or a functional group that can be converted to a hydroxy group. The crosslinked polyvinyl alcohol is more preferred because the crosslinked polyvinyl alcohol can be used even under a strongly alkaline condition.

The crosslinked polyvinyl alcohol is obtained by copolymerizing vinyl acetate and a crosslinkable monomer having a plurality of unsaturated double bonds, such as triallyl isocyanurate, and then saponifying the resultant. The mass ratio of the monomer composition of the copolymer is not particularly limited. However, in order to express sufficient hydrophilicity through subsequent reaction treatment of introducing a diol group, the ratio of the crosslinkable monomer in all monomers is set to preferably 90 mass % or less, more preferably 80 mass % or less, still more preferably 70 mass % or less. In addition, in order to secure practical mechanical strength in the case of utilizing the porous particles as a packing material for liquid chromatography, the ratio of the crosslinkable monomer in all monomers is set to preferably 10 mass % or more, more preferably 20 mass % or more, still more preferably 30 mass % or more. When the mechanical strength is insufficient, a pressure to be generated during the delivery of a mobile phase deforms the packing material to clog the column, to thereby exceed a pressure range in which an apparatus can be used, in some cases.

The hydroxy group density of the crosslinked polyvinyl alcohol obtained through saponification falls within the range of preferably from 1.2 mmol/g to 10.5 mmol/g, more preferably from 1.6 mmol/g to 9.3 mmol/g, still more preferably from 2.0 mmol/g to 8.0 mmol/g. When the density is set to this range, glycidol for introducing the diol can be sufficiently added to the particle surface, and hence appropriate hydrophilicity can be imparted to the packing material.

The hydroxy group density may be determined by calculation from an increase in mass of the porous particles occurring after a reaction with a reagent reactive with a hydroxy group. For example, a method described in Examples may be preferably used.

A general method of obtaining the crosslinkable organic polymer as porous particles is a suspension polymerization method involving suspending an oil phase obtained by mixing a monomer, a nonpolymerizable organic solvent compatible with the monomer, and a polymerization initiator in an aqueous phase to form oil droplets each having a desired size, and then heating and stirring the resultant, to thereby obtain particles. Alternatively, the following method is used: the oil phase is dropped into the aqueous phase via a porous membrane typified by a Shirasu porous glass (SPG) membrane, or microchannels formed on a quartz substrate, to form particles each having a desired size. In each of the particle formation methods, volumes occupied by the non-polymerizable organic solvent mixed into the oil phase form pores. When the thus granulated oil phase is then heated and stirred in the aqueous phase, a polymerization reaction is allowed to proceed to impart strength as a crosslinkable polymer. After the polymerization reaction, the nonpolymerizable organic solvent and the like are removed by washing with an organic solvent. Thus, the crosslinked organic polymer is obtained as a porous body.

The particles each preferably have a spherical shape.

The particle diameter of the particles is preferably from 1 μm to 30 μm in terms of volume average particle diameter in order to obtain sufficient separation performance and high sensitivity. When the viewpoint of making an excessive pressure increase less liable to occur is taken into consideration, the particle diameter is more preferably from 3 μm to 10 μm, particularly preferably from 3 μm to 5 μm in terms of volume average particle diameter.

The volume average particle diameter may be measured with a Coulter counter or an image analysis particle size distribution measurement instrument. In order to obtain a desired particle diameter, sieve classification using a mesh or particle diameter control using an air classifier may be performed.

The size of the pores forming porosity is preferably from 3 nm to 30 nm in terms of average pore size in order to achieve both separation performance and mechanical strength, and is more preferably from 10 nm to 25 nm from the viewpoint of obtaining sufficient separation performance. When the pore size is excessively small, a specific surface area is reduced and an ability to express a hydrophilic interaction is not sufficiently obtained in some cases. When the pore size is excessively large, the mechanical strength cannot be maintained and the particles are crushed by a pressure generated in the column in some cases.

The average pore size may be measured using a gas adsorption-type specific surface area measurement instrument.

The packing material for a column in one embodiment of the present invention has a structure in which a diol is fixed to the surface of each of the porous particles formed of the crosslinked organic polymer described above. The structure of the diol is preferably a structure in which adjacent carbon atoms each have one hydroxy group bonded thereto. It is more preferred that the particles each have, on the surface thereof, a structure represented by the formula (I):

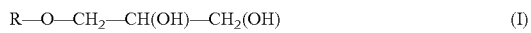

$$R\text{—}O\text{—}CH_2\text{—}CH(OH)\text{—}CH_2(OH) \qquad (I)$$

where R represents a partial structure of each of the porous particles.

The amount of the diol structure fixed to the particle surface is preferably from 0.2 mmol/g to 8 mmol/g, more preferably from 0.5 mmol/g to 4 mmol/g with respect to the mass of the porous particles.

The above-mentioned structure may be produced by allowing a compound having a hydroxy group and an epoxy group, such as glycidol, to react with the porous particles formed of the crosslinked organic polymer each having a hydroxy group on the surface thereof. The reaction of glycidol may be performed under an alkaline condition or an acidic condition.

As a mobile phase (eluent) to be used for the liquid chromatography, a mixed liquid of an aqueous solution of a volatile salt and a water-soluble organic solvent is suitably used. Examples of the volatile salt include ammonium formate, ammonium acetate, and ammonium hydrogen carbonate. The water-soluble organic solvent is preferably an alcohol compound or nitrile compound having 1 to 3 carbon atoms. The mixed liquid is preferably a combination of an aqueous ammonium formate solution and acetonitrile.

The concentration of the aqueous solution of a volatile salt is not particularly limited, but is preferably from 1 mM to 100 mM, more preferably from 5 mM to 70 mM, particularly preferably from 20 mM to 50 mM. The pH of the aqueous solution of a volatile salt is not limited as long as the pH falls within a range in which the oligonucleotides are eluted, and is preferably from 5.0 to 9.0, more preferably from 6.5 to 7.5.

A mixing ratio between the aqueous solution of a volatile salt and the water-soluble organic solvent is not particularly limited. The mixing ratio is expressed using volumes before mixing. The ratio of the water-soluble organic solvent may be increased to the extent that no problem occurs with the precipitation of a salt or the solubility of the oligonucleotides. In addition, the ratio of the water-soluble organic solvent may be decreased to the extent that the hydrophilic interaction sufficiently acts. It is generally preferred that the ratio of the water-soluble organic solvent be from 30% to 90%.

A typical separation and analysis method of the present invention is as described below.

A column packed with the above-mentioned packing material is attached to a liquid chromatograph, and the column is equilibrated by passing an appropriate eluent (mobile phase) therethrough in advance. Then, a solution obtained by dissolving the mixture of oligonucleotides serving as a sample in the same eluent is injected and liquid chromatography is performed.

A so-called gradient elution method, which involves sequentially decreasing the concentration of a water-soluble organic solvent in the eluent to be passed, may also be adopted. When the gradient elution is performed, separation between impurities incorporated during the synthesis process of oligonucleotides and a target oligonucleotide can be further facilitated. After that, the eluent passed at the time of the equilibration is passed again to equilibrate the column.

A column temperature at the time of measurement is preferably from 25° C. to 80° C., more preferably from 30° C. to 60° C., most preferably from 40° C. to 50° C.

As an apparatus for the liquid chromatography, a commercially available product may be used. Examples thereof include apparatus such as Nexera (trademark) manufactured by Shimadzu Corporation and Acquity (trademark) manufactured by Waters Corporation.

Also for the column, a commercially available product may be used as long as the commercially available product falls within the range specified above. For example, Shodex (trademark) HILICpak (trademark) VN-50 2D (2.0 mm in inner diameter×150 mm in length, particle diameter: 5 μm) manufactured by Showa Denko K.K. may be used.

For the detection of the liquid chromatography, for example, there are given an ultraviolet/visible detector (UV/Vis detector) and a mass spectrometer (MS) utilizing a mass spectrum. In the case of the ultraviolet/visible detector, a detection wavelength is, for example, 260 nm.

The ultraviolet/visible detector and the mass spectrometer may be mainly used for quantitative analysis and qualitative analysis, respectively, and may also be used in combination.

The packing material to be used in one embodiment of the present invention has a property of being stable under an alkaline condition. Accordingly, after the separation and analysis by the liquid chromatography have been performed, the column can be washed by passing an alkaline solution therethrough. Thus, a protein, an oligonucleotide, a side reaction product, or the like contaminating the column and adsorbed onto the packing material can be decomposed and removed, and the inside of the column can be sterilized. Therefore, the packing material is advantageous when the liquid chromatography is performed for the purpose of fractionating oligonucleotides.

The passing of the alkaline solution may be performed before or after the liquid chromatography is performed, as required.

In general, a packing material using silica gel as a base cannot be used under the condition of a pH of 8 or more because the silica gel is dissolved. For this reason, an alkaline solution cannot be used. The base of the packing material to be used in one embodiment of the present invention is formed of the crosslinked organic polymer, and hence an alkaline solution having a pH appropriate for the property of the crosslinked organic polymer to be used can be used. In particular, the packing material using the crosslinked polyvinyl alcohol as its base is not deteriorated by a generally used alkaline solution, and hence the alkaline solution can be used for column washing or the like.

The alkaline solution to be used for the washing is not particularly limited as long as the alkaline solution shows an alkalinity of a pH of from 10.0 to 13.0. In consideration of the effect and economic efficiency of the washing, a 0.01 M to 0.1 M aqueous sodium hydroxide solution is suitable.

The reason why a higher degree of separation is achieved in the case of using the packing material obtained by the diol structure fixed to the surface of each of the porous particles formed of the crosslinked organic polymer than in the case of using the packing material using silica gel has yet to be elucidated. However, a column using silica gel may be affected by, for example, simultaneous action of a weak ionic interaction resulting from silanol, which may possibly cause a degradation in separation in hydrophilic interaction chromatography utilizing a difference in hydrophilicity.

EXAMPLES

The present invention is specifically described below by way of Example and Comparative Example.

Production of Column

A column used in Example was produced as described below.

(1) Production of Base

A homogeneously mixed liquid formed of 100 g of vinyl acetate, 150 g of triallyl isocyanurate, 100 g of butyl acetate, 25 g of n-decane, and 5 g of 2,2-azobisisobutyronitrile, and an aqueous solution obtained by dissolving 12 g of polyvinyl alcohol (PVA224 manufactured by Kuraray Co., Ltd.) and 18 g of disodium hydrogen phosphate in 1,200 mL of water were placed in a 5 L three-necked flask with a reflux condenser, and the contents were stirred for 10 minutes. Then, while being stirred under a nitrogen gas stream, the contents were polymerized at 60° C. for 16 hours to provide a particulate copolymer. The copolymer was filtered, washed with warm water at 50° C., washed with acetone, and then dried. Then, the copolymer was placed, together with 3 L of a 1 M aqueous sodium hydroxide solution, in a 5 L three-necked flask with a reflux condenser, a nitrogen gas inlet tube, and a stirrer, and the contents were stirred under a nitrogen stream at 15° C. for 20 hours to saponify the copolymer. The resultant was filtered, washed with water, dried, and subjected to air classification treatment to provide porous particles formed of a crosslinked polyvinyl alcohol copolymer. The polyvinyl alcohol copolymer obtained through the saponification had a hydroxy group density of 2.1 mmol/g. Particle diameter measurement was performed with an image analysis particle size distribution measurement apparatus (FPIA3000 manufactured by Sysmex Corporation), and as a result, a volume average particle diameter was found to be 4.8 μm. In addition, an average pore size measured with a gas adsorption-type specific surface area measurement apparatus (BELSORP (trademark)-mini manufactured by BEL Japan, Inc.) was 13 nm.

The hydroxy group density was measured by the following procedure.

About 2 g of a sample (polyvinyl alcohol copolymer) is vacuum-dried at 60° C. for 6 hours, and then accurately measured for its mass with a precision balance. The whole amount of the weighed sample, and a mixed liquid of 17 mL of acetic anhydride and 33 mL of pyridine are quickly loaded into a 50 mL Erlenmeyer flask, and then an Allihn condenser is fitted to an upper portion of the Erlenmeyer flask. Further, a nitrogen gas is quietly blown from an upper portion of the condenser to purge air in the flask. Under this state, while stirred with a magnetic stirrer, the whole is heated in an oil bath at 90° C. for 16 hours. After the completion of the heating, a total of 15 mL of methanol is added in small portions, and the sample is filtered with a glass filter. Further, the resultant is washed with 90 mL of methanol, and then vacuum-dried at 60° C. for 6 hours. The sample after the drying is accurately measured for its mass with a precision balance, and a difference between the mass and that before the reaction with acetic anhydride is calculated. An acetic acid fragment ($CH_3CO-$: molecular weight 43) added as an ester to a hydroxy group of the base corresponds to an increase in mass, and hence, on the basis of this, a hydroxy group density per mass of the sample (unit: mmol/g) is calculated.

(2) Introduction of Diol 10 g of the porous particles obtained in the section (1), 10 g of glycidol, 1 g of potassium tert-butoxide, and 100 mL of diethylene glycol dimethyl ether were placed in a separable flask, and stirred at 60° C. for 20 hours to add glycidol to the porous particles. The resultant particles were washed with water and methanol, and then dried to provide a packing material 1. The addition amount of glycidol was calculated by mass measurement, and was found to be 2 mmol/g per mass of the porous particles.

(3) Packing into Column Housing

The obtained packing material 1 was dispersed in water to provide a slurry, and the slurry was packed under pressure into a column housing made of PEEK having an inner diameter of 2.0 mm and a length of 150 mm (manufactured by Tomoe Works Co., Ltd.) through solvent delivery at a constant pressure of 15 MPa for 10 minutes with the use of a solvent delivery pump. Thus, a column was obtained.

Example 1

(1) Step of Equilibrating Column

An apparatus used was a liquid chromatograph/mass spectrometer manufactured by Shimadzu Corporation and including a system controller CBM-20A, a degasser DGU-20A5R, a solvent delivery unit LC-30AD (two units for adapting to a high-pressure gradient), an autosampler SIL-30AC, a column oven CTO-20AC, a photodiode array detector SPD-M20A, and a triple quadrupole mass spectrometer LCMS-8030. A column temperature was set to 40° C., and the column was equilibrated by passing 2 mL or more of 50 mM aqueous ammonium formate solution/acetonitrile=38/62 (volume ratio before mixing) therethrough as an eluent at 0.2 mL/min.

(2) Step of Preparing Sample for Analysis

A 20-mer synthetic oligonucleotide purchased from Eurofins Genomics K.K. (product name: Standard Oligo 50 nmol-scale salt-free grade; base sequence represented by SEQ ID NO: 1 (5'-ATACCGATTAAGCGAAGTTT-3')) was dissolved in the eluent to prepare a sample for analysis so that the concentration of the synthetic oligonucleotide was 1 mg/mL.

(3) Step of Injecting Synthetic Oligonucleotide

1 μL of the prepared sample for analysis was injected into the column equilibrated in the step (1).

(4) Step of Separating and Eluting Synthetic Oligonucleotide and Non-Full-Length Impurities The eluent was delivered with the following gradient: the ratio of acetonitrile was decreased to 56% (vol % before mixing. The same applies hereinafter.) in the first 10 minutes in a linear gradient. The ratio of acetonitrile was then kept at 56% until 20 minutes to separate and elute the synthetic oligonucleotide and impurities. The ratio of acetonitrile was returned to 62% in a period from 20.01 minutes to 25 minutes, so that the column was equilibrated and made ready for the next analysis.

Detection was performed as described below. First, the range of from 190 nm to 350 nm was monitored with the photodiode array detector. A chromatogram was displayed at 260 nm. Further, the synthetic oligonucleotide and non-full-length impurities were monitored by a selected ion monitoring (SIM) method through the use of the mass spectrometer arranged immediately after the photodiode array detector.

The results were as shown in FIG. 1. Specifically, in both a UV chromatogram and a mass chromatogram, a peak of the 20-mer synthetic oligonucleotide was observed at a retention time of 18.5 minutes, and peaks of 2-mer to 19-mer non-full-length impurities were observed in molecular weight order in an earlier period of from 2 minutes to 17 minutes.

2 mL of a 0.1 N aqueous sodium hydroxide solution was passed through the column after the analysis at 0.2 mL/min to wash the column. After that, the column was equilibrated, and the analysis of the synthetic oligonucleotide was performed again. As a result, there were no changes in column pressure and analysis results.

Comparative Example 1

The synthetic nucleotide was separated in the same manner as in Example 1 except that YMCpak Diol-120-NP manufactured by YMC Co., Ltd. (2.0 mm in inner diameter× 150 mm in length, particle diameter: 5 μm) was used as a column. This column uses a packing material in which a diol is bonded to silica gel serving as a base.

Figure 2:
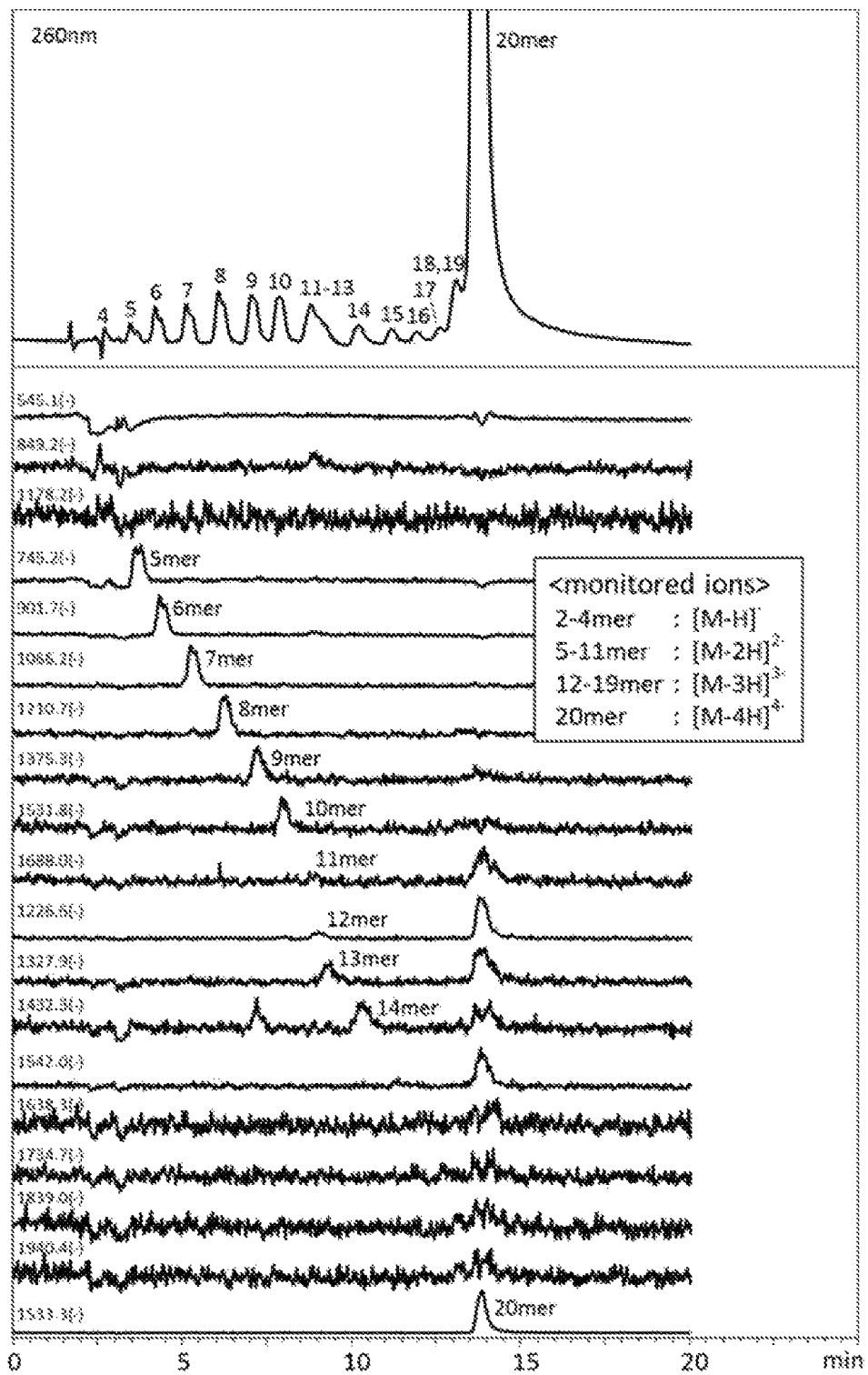
FIG. 2 are an ultraviolet detection (wavelength: 260 nm) chromatogram and a mass spectrometric mass chromatogram obtained in Comparative Example 1.

The results were as shown in FIG. 2. Specifically, in both a UV chromatogram and a mass chromatogram, a peak of the synthetic oligonucleotide was observed at a retention time of 14 minutes. In the UV chromatogram, peaks of 2-mer to 19-mer non-full-length impurities were observed in molecular weight order in an earlier period of from 2 minutes to 13.5 minutes. As compared to Example 1, the 5-mer to the 9-mer had poor peak shapes, and the 11-mer to the 13-mer were poorly separated. In the mass chromatogram, as compared to Example 1, all peaks had poor signal-to-noise ratios, and the 15-mer to the 19-mer were not able to be detected.

This column was a column using silica gel as its base, and hence washing with an alkaline aqueous solution was not performed.

The invention claimed is:

1. A method of separating and analyzing a mixture of oligonucleotides, including performing liquid chromatography using a column packed with a packing material obtained by fixing a diol to a surface of each of porous particles consisting of a crosslinked organic polymer selected from the group consisting of a (meth)acrylic resin and a crosslinked polyvinyl alcohol, wherein a structure of the diol includes a structure represented by the following formula (I):

R—O—CH$_2$—CH(OH)—CH$_2$(OH)    (I)

where R represents a partial structure of each of the porous particles, and wherein R consists of a crosslinked organic polymer selected from the group consisting of a (meth)acrylic resin and a crosslinked polyvinyl alcohol.

2. The method according to claim 1, wherein the crosslinked organic polymer is crosslinked polyvinyl alcohol.

3. The method according to claim 1, wherein a mobile phase of the liquid chromatography is a mixed liquid of an aqueous solution of a volatile salt and a water-soluble organic solvent.

4. The method according to claim 1, further including detecting an eluted component separated through the column with an ultraviolet/visible detector and/or a mass spectrometer.

5. The method according claim 1, wherein the liquid chromatography is performed by gradient elution of a mobile phase.

6. The method according claim 1, further including, before or after the performing liquid chromatography, a step of washing the column by passing an alkaline solution having a pH of from 10.0 to 13.0 through the column.

7. The method according to claim 1, wherein the oligonucleotides are synthetic oligonucleotides.

8. The method according to claim 6, wherein the crosslinked organic polymer is crosslinked polyvinyl alcohol.

* * * * *